United States Patent
Choi et al.

(10) Patent No.: US 11,813,285 B2
(45) Date of Patent: *Nov. 14, 2023

(54) STABLE PHARMACEUTICAL COMPOSITION COMPRISING ESOMEPRAZOLE AND SODIUM BICARBONATE

(71) Applicant: CHONG KUN DANG PHARMACEUTICAL CORP., Seoul (KR)

(72) Inventors: Jong Seo Choi, Yongin-Si (KR); Min Soo Kim, Yongin-Si (KR); Shin Jung Park, Yongin-Si (KR); Jong Lae Lim, Yongin-Si (KR)

(73) Assignee: CHONG KUN DANG PHARMACEUTICAL CORP., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/965,748

(22) PCT Filed: Jan. 9, 2019

(86) PCT No.: PCT/KR2019/000309
§ 371 (c)(1),
(2) Date: Jul. 29, 2020

(87) PCT Pub. No.: WO2019/146937
PCT Pub. Date: Aug. 1, 2019

(65) Prior Publication Data
US 2021/0030786 A1    Feb. 4, 2021

(30) Foreign Application Priority Data
Jan. 29, 2018    (KR) .................. 10-2018-0010980

(51) Int. Cl.
*A61K 33/00* (2006.01)
*A61K 31/4439* (2006.01)

(52) U.S. Cl.
CPC .......... *A61K 33/00* (2013.01); *A61K 31/4439* (2013.01)

(58) Field of Classification Search
CPC ..................... A61K 33/00; A61K 31/4431
See application file for complete search history.

(56) References Cited

U.S. PATENT DOCUMENTS

| | | |
|---|---|---|
| 6,183,776 B1 | 2/2001 | Depui et al. |
| 6,369,085 B1 | 4/2002 | Cotton et al. |
| 2005/0239845 A1 | 10/2005 | Proehl et al. |
| 2005/0266071 A1 | 12/2005 | Olmstead et al. |
| 2007/0053981 A1 | 3/2007 | Blychert et al. |
| 2009/0092658 A1 | 4/2009 | Hall et al. |
| 2010/0029654 A1 | 2/2010 | Pasinetti |
| 2012/0121664 A1 | 5/2012 | Pettersson et al. |
| 2012/0128764 A1 | 5/2012 | Venkatesh et al. |
| 2014/0271853 A1 | 9/2014 | Hall et al. |
| 2015/0044303 A1 | 2/2015 | Olmstead et al. |
| 2021/0030687 A1 | 2/2021 | Choi et al. |
| 2022/0233514 A1 | 7/2022 | Choi et al. |

FOREIGN PATENT DOCUMENTS

| | | |
|---|---|---|
| CN | 1183047 A | 5/1998 |
| CN | 101002769 A | 7/2007 |
| CN | 101036633 A | 9/2007 |
| CN | 102078616 A | 6/2011 |
| CN | 102397277 A | 4/2012 |
| CN | 103599082 A | 2/2014 |
| CN | 103784414 A | 5/2014 |
| CN | 103845734 A | 6/2014 |
| CN | 103860584 A | 6/2014 |
| CN | 103006691 B | 10/2014 |
| CN | 104523746 A | 4/2015 |
| CN | 204428461 U | 7/2015 |
| EP | 0496437 * | 4/1987 |
| EP | 3236952 A1 | 11/2017 |
| JP | H11501950 A | 2/1999 |
| JP | 2003-073270 A | 3/2003 |
| JP | 2006/505566 A | 2/2006 |
| JP | 2006-528198 A | 12/2006 |
| JP | 2007526319 A | 9/2007 |
| JP | 2008/500365 A | 1/2008 |
| JP | 2008-504372 A | 2/2008 |
| JP | 2008-512453 A | 4/2008 |
| JP | 2009534441 A | 9/2009 |
| JP | 2011-512416 A | 4/2011 |
| JP | 2011530569 A | 12/2011 |
| JP | 2016-509061 A | 3/2016 |

(Continued)

OTHER PUBLICATIONS

ClinicalTrials.gov Identifier: NCT01471925.*
Approval package NDA21153S-008(Astrazeneca, Jan. 9, 2004).*
International Search Report for PCT Application No. PCT/KR2020/009250, dated Oct. 15, 2020.
"A randomized, open-label, multiple-dose, and three-way crossover clinical trial to compare pharmacokinetics and safety of CKD-381 and D026 in healthy male subjects", Chong Kun Dang Pharm., excerpt from clinical trial report.
Eso Duo Tablet Product Insert with partial English translation.

(Continued)

*Primary Examiner* — Shirley V Gembeh
(74) *Attorney, Agent, or Firm* — Foley Hoag LLP; David P. Halstead; Benjamin A. Vaughan

(57) ABSTRACT

The present invention relates to a stable pharmaceutical composition comprising omeprazole, its enantiomer, or its pharmaceutically acceptable salt, and sodium bicarbonate. Specifically, the present invention relates to a pharmaceutical composition with improved stability comprising a low dose of sodium bicarbonate, so that it has improved dissolution rate and bioavailability and also reduces side effects resulting from a high dose of sodium bicarbonate.

4 Claims, 5 Drawing Sheets

(56) References Cited

FOREIGN PATENT DOCUMENTS

| | | | |
|---|---|---|---|
| JP | 7003279 B2 | 1/2022 | |
| KR | 10-0115254 B | 12/1995 | |
| KR | 10-1996-0003605 B1 | 3/1996 | |
| KR | 100274698 B1 | 12/2000 | |
| KR | 10-2002-0089322 A | 11/2002 | |
| KR | 100384960 B1 | 8/2003 | |
| KR | 10-2004-0047771 A | 6/2004 | |
| KR | 10-2004-0099265 A | 11/2004 | |
| KR | 2005/0061647 A | 6/2005 | |
| KR | 100679767 B1 | 2/2007 | |
| KR | 10-2010-0066742 A | 6/2010 | |
| KR | 10-2011-0079641 A | 7/2011 | |
| KR | 10-2011-0123178 A | 11/2011 | |
| KR | 101104349 B1 | 1/2012 | |
| KR | 20130115593 A | 10/2013 | |
| KR | 10-2015-0083255 A | 7/2015 | |
| KR | 20160020625 A | 2/2016 | |
| KR | 10-2016-0082169 A | 7/2016 | |
| KR | 10-2016-0124368 A | 10/2016 | |
| KR | 2017/0076494 A | 7/2017 | |
| KR | 10-2017-0126915 A | 11/2017 | |
| KR | 10-2017-0136771 A | 12/2017 | |
| KR | 10-2018-0010987 A | 1/2018 | |
| KR | 20180011624 A | 2/2018 | |
| KR | 20180098744 A | 9/2018 | |
| KR | 20190003312 A | 1/2019 | |
| KR | 20190037182 A | 4/2019 | |
| KR | 10-2006777 B1 | 10/2019 | |
| KR | 10-2080023 B1 | 2/2020 | |
| KR | 10-2146395 | 8/2020 | |
| WO | WO1997025066 A1 | * | 7/1997 |
| WO | WO-2001/051050 A1 | 7/2001 | |
| WO | WO-2003/009846 A1 | 2/2003 | |
| WO | WO-2005/092297 A2 | 10/2005 | |
| WO | WO-2008110070 A1 | 9/2008 | |
| WO | WO-2016/024822 A1 | 2/2016 | |
| WO | WO-2017-122212 A1 | 7/2017 | |
| WO | WO-2019/146937 A1 | 8/2019 | |
| WO | WO-2019/147094 A1 | 8/2019 | |
| WO | WO-2020/040438 A1 | 2/2020 | |

OTHER PUBLICATIONS

Excerpt from "Pharmaceutical Dosage Forms" relating to Granulation Processes with partial English translation, published Feb. 15, 2013, modified Feb. 15, 2015 (with partial English translation).
Excerpt from Korean Pharmacopia relating to dissolution test method (with partial English translation).
Experimental Report of Comparative Dissolution Tests on Eso Duo Tablets (with partial English translation).
Experimental Report of Comparative Stability of Chong Kun Dang Pharmecuritcals Corp. omeprazole sulfone tablets with Genuonesciences omeprazole sulfone tablets, (with English translation), 16 pages.
Experimental Report of Comparative test of FTC dissolution based on the amount of sodium bicarbonate in esomeprazole granule (with partial English translation).
Experimental Report of Comparative test of FTC dissolution of esomeprazole/sodium bicarbonate formulations (with partial English translation).
Experimental Report of FTC Dissolution Test of Eso Duo Tab. (40/800 mg) (with partial English translation).
Ganaflux Product Insert with partial English translation.
Gardner et al., "Integrated Acidity and the Pathophysiology of Gastroesophageal Reflux Disease", The American Journal of Gastroenterology, vol. 96, No. 5, 2001, pp. 1363-1370.
Information Sheet on Esoduo Tabs 20/800 mg, permit date Apr. 30, 2018, with English machine translation.
Information Sheet on Ganaflux Tab 40/1100 mg, date of approval Jun. 19, 2015 (with partial English translation).
Kim et al. "The safety, pharmacodynamics, and pharmacokinetics of immediate-release formulation containing esomeprazole 20 mg/sodium biocarbonate 800 mg in healthy adult male", Drug Design, Development and Therapy 2019:13, pp. 3151-3159.
Lee et al., "Effect of Other Medications on the Stability of Omeprazole in Aqueous Solution for the Peptic Ulcer Disease", Journal of the Korean Society of Industrial Science and Technology, vol. 10, No. 11, pp. 3494-3499, 2009 (with English abstract).
Mishra et al. "Formulation, Development and Evaluation of an Immediate Release Buffer Tablet of Omeprazole", Pharma Science Monitor 7(2), Apr-Jun. 2016, pp. 270-281.
Newspaper Article from MedicalObserver.com describing Eso Duo Tab, dated Jul. 23, 2018, updated Mar. 24, 2021 (with partial English translation).
Newspaper Article from MedicalTimes.com describing Chong Kun Dang combination of esomeprazole and sodium bicarbonate, dated Jan. 26, 2018, accessed Mar. 26, 2021 (with partial English translation).
Newspaper Article from Yakup.com describing Ganaflux Tab (40-1100 mg), accessed Mar. 26, 2021 (with partial English translation).
Tutuian et al., "The acidity index: a simple approach to the measurement of gas acidity", Aliment Pharmacol Ther 2004; 19: pp. 443-448.
Yacyshyn et al., "The Clinical Importance of Proton Pump Inhibitor Pharmacokinetics", Digestion 2002; 66: pp. 67-78.
Howden., "Immediate-Release Omeprazole/Sodium Bicarbonate," Gastroenterology & Hepatology, 2(5): 386 (2006).
International Search Report for PCT Application No. PCT/KR2019/009371 dated Oct. 25, 2019.
Xingguo, "Microcarrier Drug Delivery System", Wuhan, Huazhong University of Science and Technology Press, 4 pages (2009) (English translation).
Xingguo, "Microcarrier Drug Delivery System", Wuhan, Huazhong University of Science and Technology Press, 4 pages (2009).
Marketing Materials for OPADRYL amb II, published by Colorcon, 2 pages.
Levina et al., "The Influence of Film Coatings on Performance of Hypromellose Matrices", published by Colorcon, dated Feb. 5, 2020, 3 pages.
Protocol for Testing and Analysis of Nexoduo tablet 20/80mg, dated Oct. 5, 2021 (with English translation), 3 pages.
Experimental Report of Comparative Stability of Chong Kun Dang Pharmaceuticals Corp. omeprazole sulfone tablets with Genuonesciences omeprazole sulfone tablets, (with English translation), 16 pages.
Rowe et al., "Handbook of Pharmaceutical Excipients" Sixth Edition, Pharmaceutical Press, published 2009.
Certificate of Analysis for Opadry Amb II High Performance Moisture Barrier Film Coating 88A5400358 Pink, dated Mar. 30, 2020, 6 pages.

* cited by examiner

[Fig. 1a]
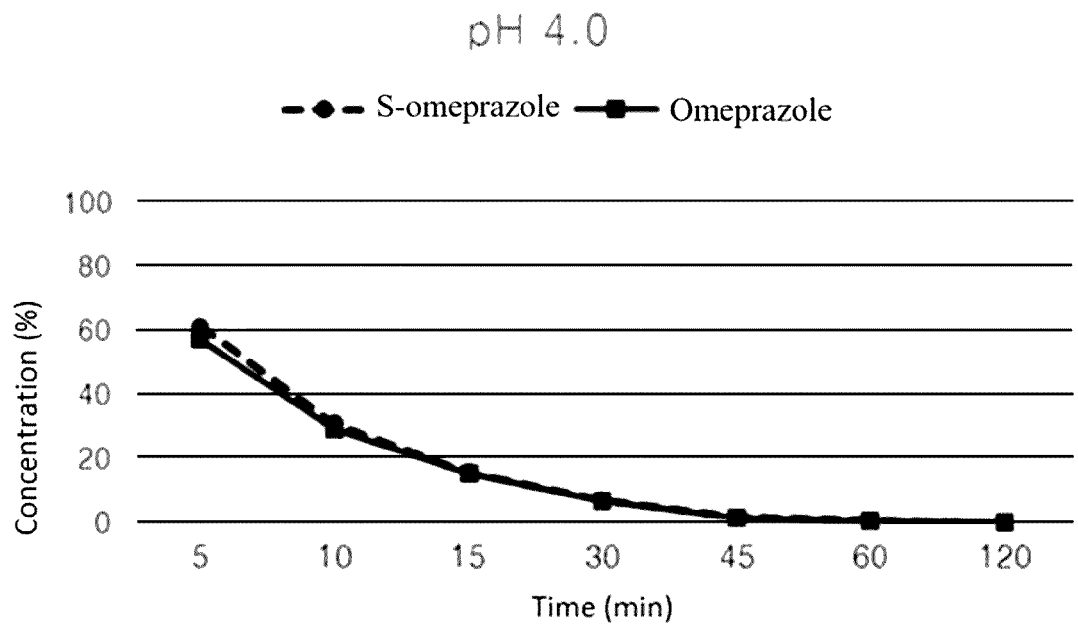
[Fig. 1b]
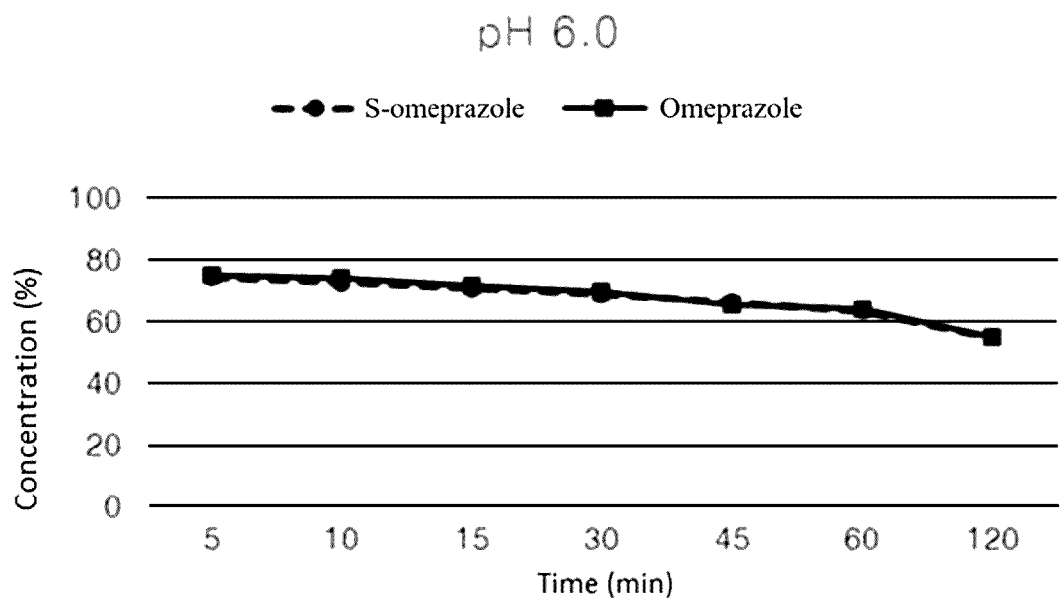

[Fig. 1c]
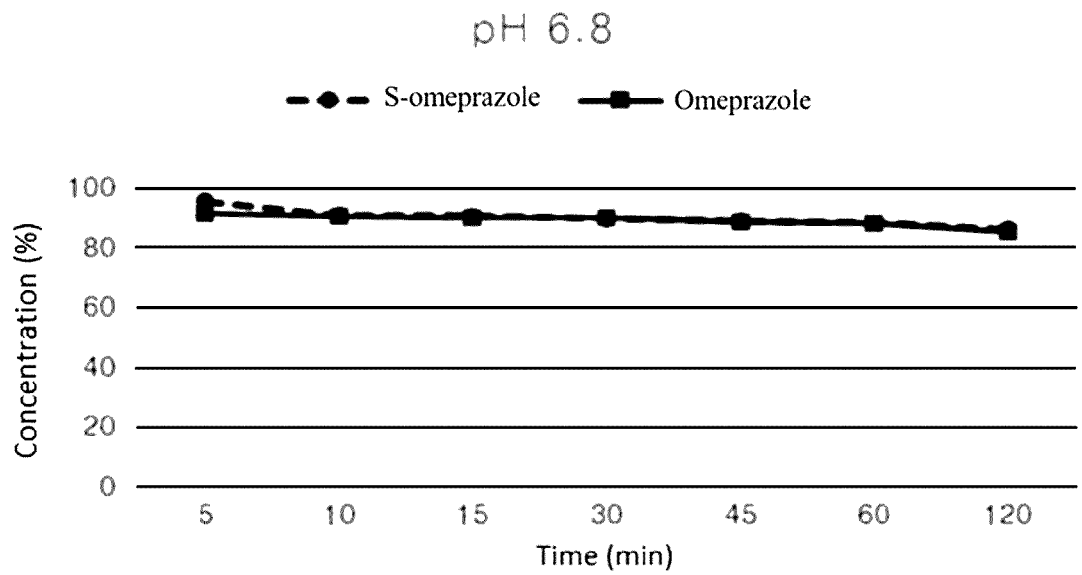
[Fig. 1d]
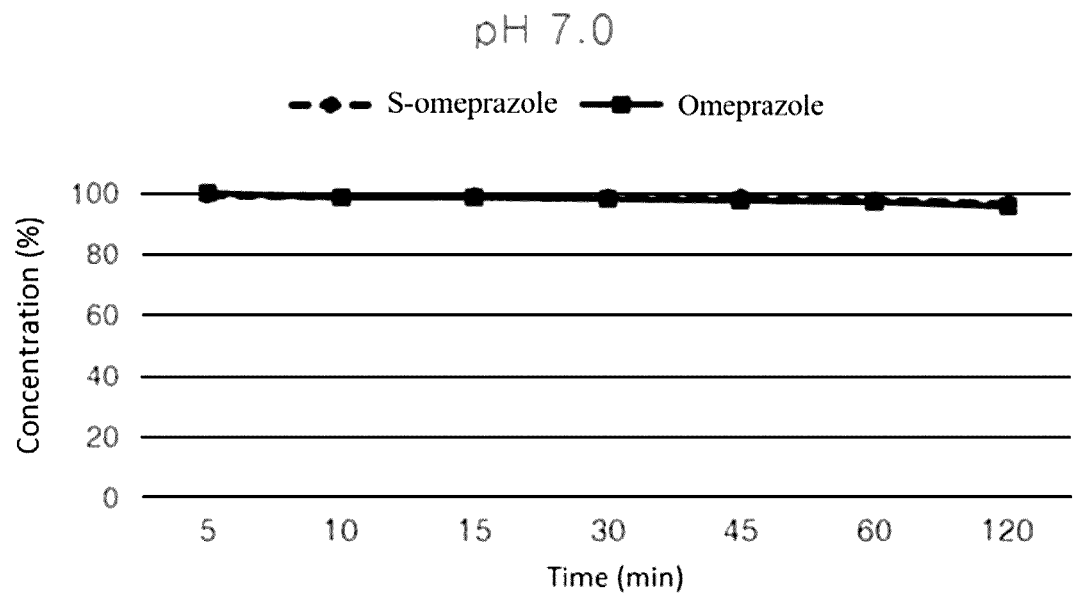

[Fig. 1e]
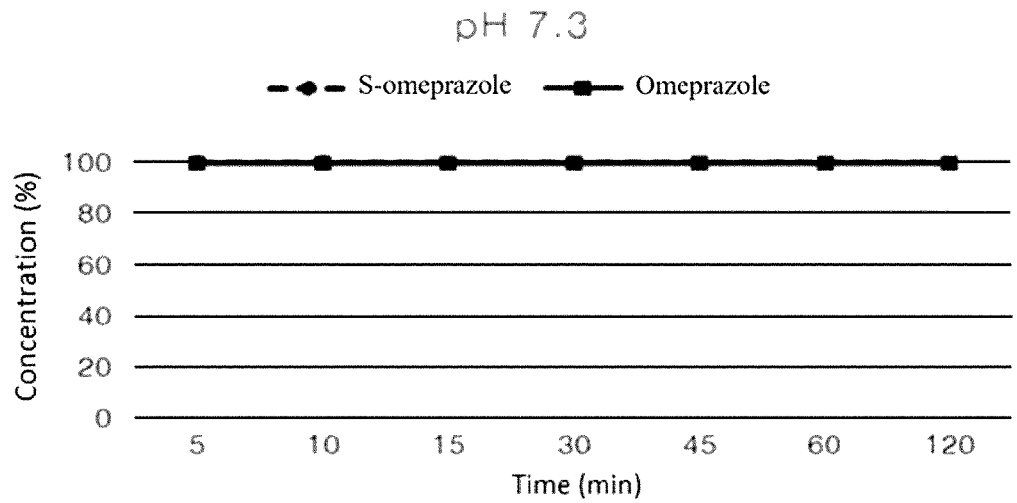
[Fig. 1f]
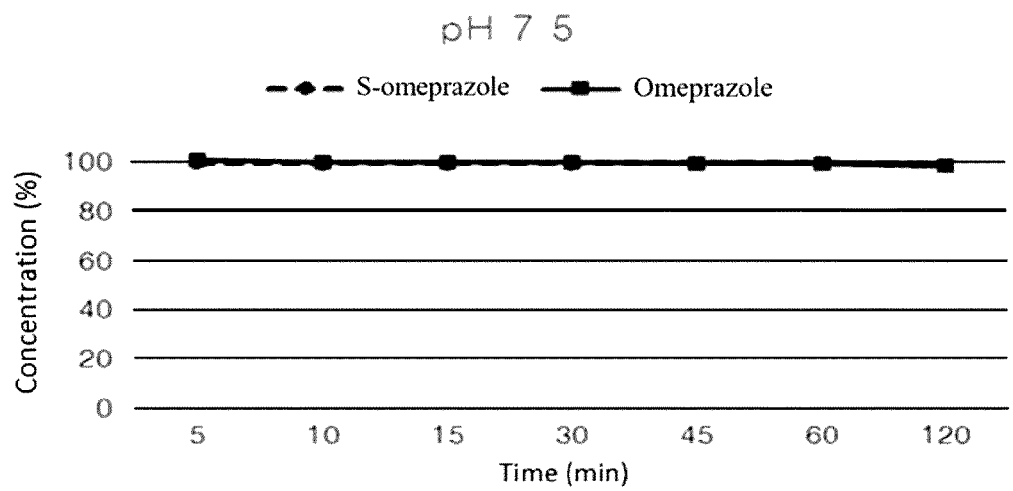
[Fig. 1g]
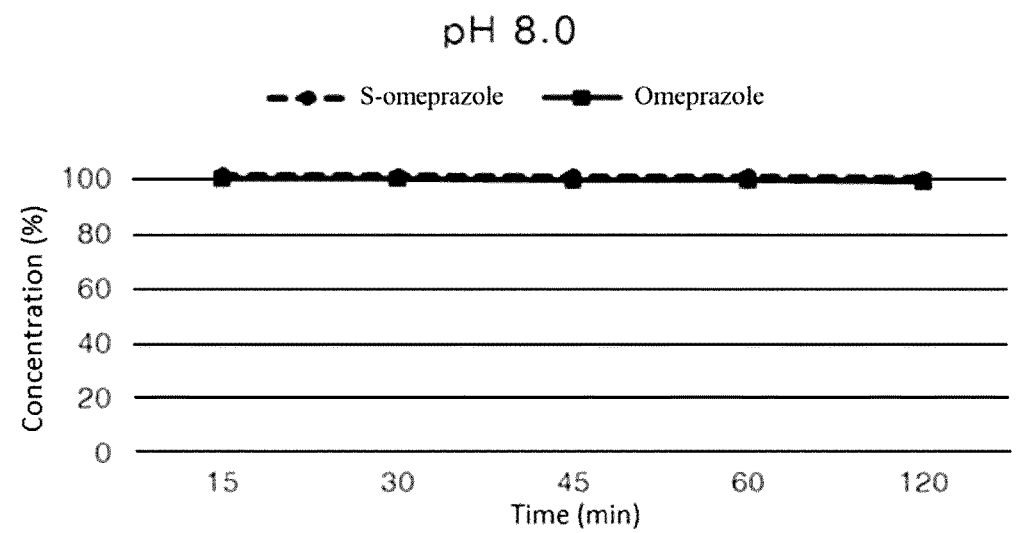

[Fig. 2]
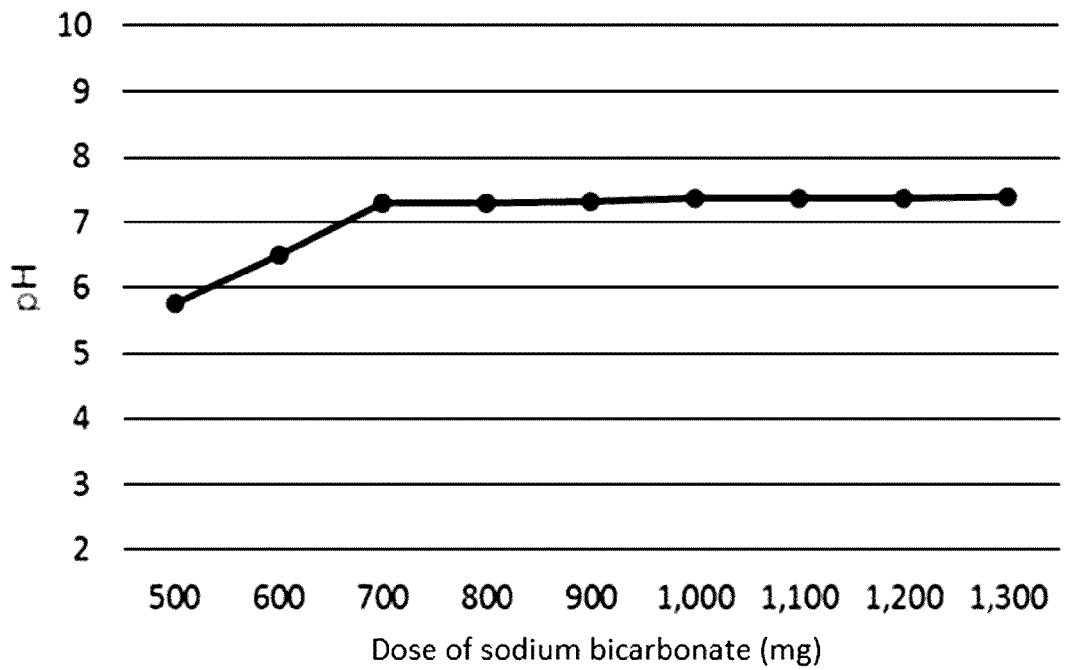
[Fig. 3]
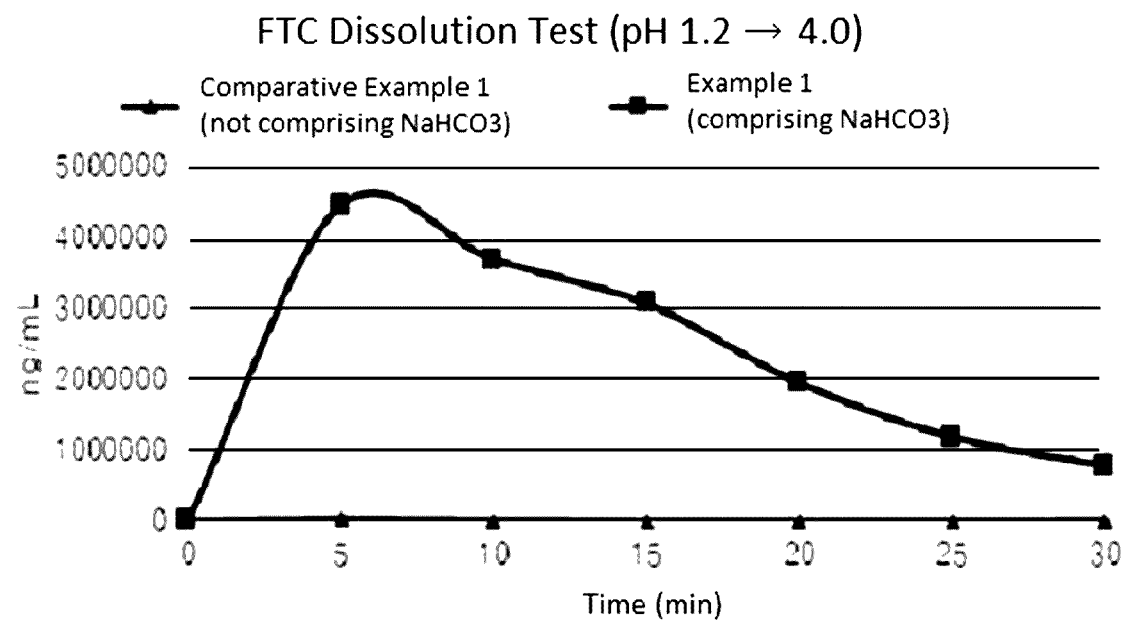

[Fig. 4]
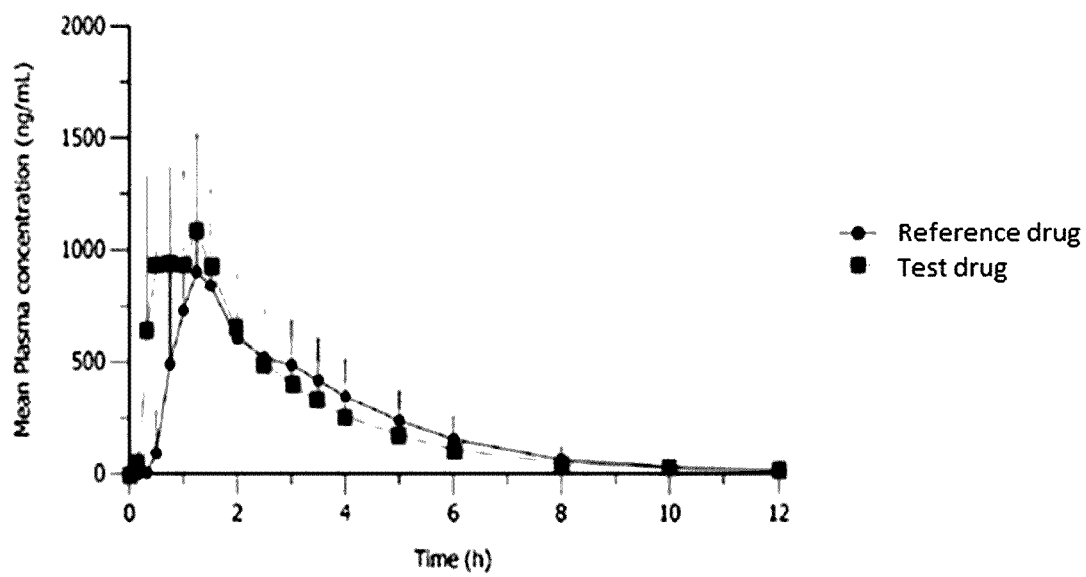
[Fig. 5]
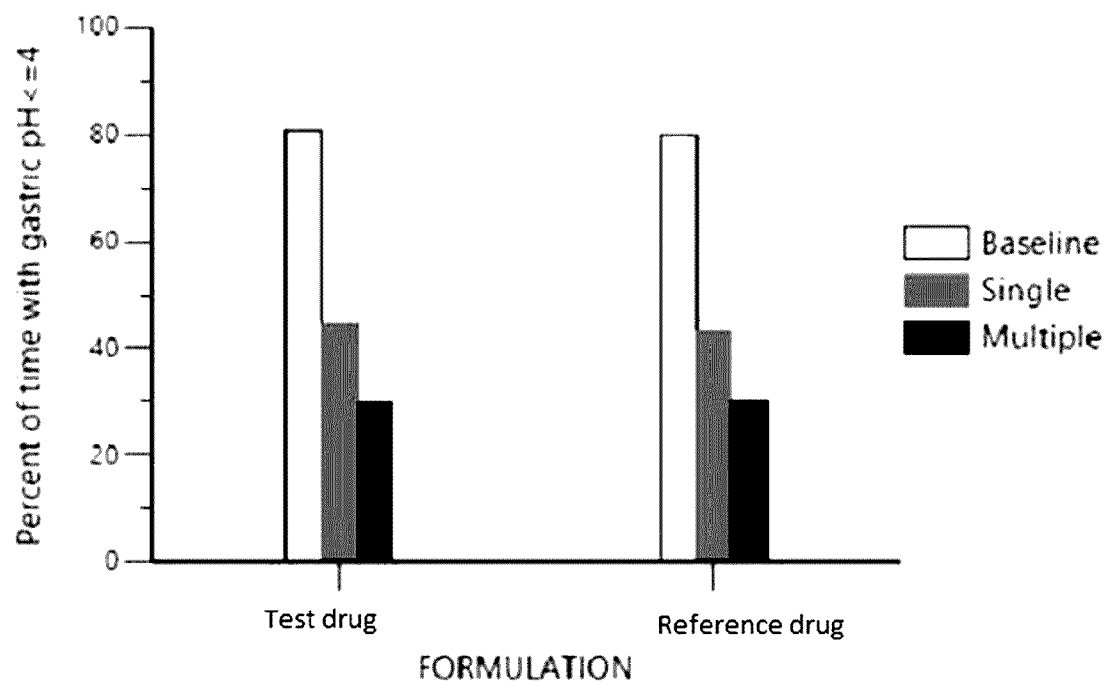

STABLE PHARMACEUTICAL COMPOSITION COMPRISING ESOMEPRAZOLE AND SODIUM BICARBONATE

RELATED APPLICATIONS

This application is the U.S. National Phase of International Patent Application No. PCT/KR2019/000309, filed Jan. 9, 2019, which claims the benefit of priority to Korean Patent Application No. KR 10-2018-0010980, filed Jan. 29, 2018. International Patent Application No. PCT/KR2019/000309 is incorporated herein by reference in its entirety.

TECHNICAL FIELD

The present invention relates to a stable pharmaceutical composition comprising omeprazole, its enantiomer, or its pharmaceutically acceptable salt, and sodium bicarbonate. Specifically, the present invention relates to a pharmaceutical composition with improved stability comprising a low dose of sodium bicarbonate, so that it has improved dissolution rate and bioavailability and also reduces side effects resulting from a high dose of sodium bicarbonate.

BACKGROUND ART

Omeprazole has a chemical name of 5-methoxy-2-[(4-methoxy-3,5-dimethyl-2-pyridinyl)methyl]sulfinyl-1H-benzimidazol. Omeprazole exists in the two types of isomers: R-isomer and S-isomer. S-isomer is known for being remarkably excellent in terms of the treatment effect and side effects in comparison with R-isomer. S-isomer refers to (S)-5-methoxy-2-[(4-methoxy-3,5-dimethyl-2-pyridinyl)-methyl]sulfinyl-1H-benzimidazol, which is commonly called esomeprazole.

Esomeprazole is a representative proton-pump inhibitor (PPI) which is used for the treatment of dyspepsia, peptic ulcer disease, gastroesophageal reflux disease, Zollinger-Ellison syndrome, and the like.

It is well known in the art that omeprazole, especially, esomeprazole, is prone to degradation or transformation in acidic and neutral media. More particularly, esomeprazole is known to have less than 10 minutes of a degradation half-life in an aqueous solution having 3 or lower of pH. As such, decomposition of esomeprazole is catalyzed by an acidic compound, and also affected by moisture, heat, organic solvents, and light.

Thus, there have been a lot of demands on a stable esomeprazole formulation. In order to solve the stability issue, Korean Patent No. 384960 discloses a method of preparing a pellet comprising a magnesium salt of esomeprazole, followed by enteric coating, adding excipients, and formulating as a tablet. The formulation as prepared based on the method described above is currently being marketed under the trade name of Nexium®.

However, an enteric-coated tablet such as Nexium® is not suitable for the treatment of diseases requiring immediate therapeutic effect after administration, such as gastric acid-related diseases, because it was designed to be dissolved and absorbed in the intestine while not causing immediate absorption in the stomach.

Korean Patent No. 1104349 discloses an enteric-coated tablet and capsule wherein the insufficiency of the stability and properties of omeprazole was improved by preparing a solid dispersion formulation with magnesium oxide and povidone.

Korean Patent Publication No. 10-1996-0003605 discloses a method for preparing a solid dispersion formulation comprising omeprazole as an active ingredient wherein beta-cyclodextrin and sodium hydroxide are added as a stabilizing ingredient. However, the invention as described in the above undesirably uses sodium hydroxide which is harmful to human body. The process of preparing the solid dispersion comprises dissolving the active ingredient, omeprazole, in a solvent, wherein a special stabilizer such as sodium hydroxide is required to stabilize omeprazole.

To solve these problems, Korean Patent No. 679767 discloses a method of using a buffering agent such as sodium bicarbonate for omeprazole.

However, the use of a large amount of sodium bicarbonate has the disadvantage of reducing the efficacy of omeprazole and causing side effects. In particular, when sodium bicarbonate is administered in a large amount, the stomach may be swollen to further increase pain in a critical patient. The absorption of sodium bicarbonate may induce burping while the burping may cause gastric acid to move upward, whereby deteriorating gastroesophageal reflux disease. Further, patients with symptoms such as hypertension or heart failure should avoid the intake of sodium which may result in hypertensive symptoms. As such, it is not appropriate to administer a large amount of sodium bicarbonate to patients with these symptoms. In addition, the administration of a large amount of sodium bicarbonate to patients with various complications is at risk of causing metabolic alkalemia. Moreover, because buffering agents that alter pH of the stomach and urine may affect an absorption, distribution, and metabolic process of a drug, the use of a large amount of sodium bicarbonate with omeprazole requires more attention.

DISCLOSURE OF INVENTION

Technical Problem

The inventors have developed a formulation comprising sodium bicarbonate to stabilize omeprazole which is unstable at a low pH. In order to solve the problem requiring a large amount of sodium bicarbonate to increase the pH value in the stomach, a pharmaceutical composition using a low dose of sodium bicarbonate to provide improved dissolution rate and bioavailability has been developed to arrive at the present invention.

Solution to Problem

The present invention relates to a pharmaceutical composition with improved stability comprising omeprazole, its enantiomer, or its pharmaceutically acceptable salt, and sodium bicarbonate.

Omeprazole may be in any enantiomer type of S-isomer or R-isomer, preferably, S-isomer, i.e., esomeprazole.

The term "a pharmaceutically acceptable salt" as used herein may be, but is not limited to, a metal salt comprising sodium, potassium, calcium, magnesium, zinc, lithium, etc., or an ammonium salt. Among them, a magnesium salt is preferable.

Omeprazole, its enantiomer, or its pharmaceutically acceptable salt may be in a solvate comprising hydrates such as monohydrate, dihydrate, or trihydrate, and may be in an amorphous or crystal form.

The pharmaceutical composition according to the present invention may comprise 15 to 50 parts by weight, preferably, 20 to 40 parts by weight of sodium bicarbonate, based on 1 part by weight of omeprazole in omeprazole, its enantiomer, or its pharmaceutically acceptable salt.

The present invention relates to a pharmaceutical composition comprising omeprazole, its enantiomer, or its pharmaceutically acceptable salt, and sodium bicarbonate wherein omeprazole, its enantiomer, or its pharmaceutically acceptable salt is comprised in 20 mg or 40 mg based on the weight of omeprazole, and sodium bicarbonate is comprised in 600 to 1000 mg.

When the dose of sodium bicarbonate is 600 mg or more, the pH of gastric juice turns into the neutral condition, so that the decomposition of omeprazole may be prevented. In case of 1,000 mg or more, there are few changes in the pH of gastric juice.

Preferably, the dose of sodium bicarbonate may be 700 to 900 mg, more preferably, 800 mg.

The present invention relates to a pharmaceutical composition comprising esomeprazole magnesium trihydrate and sodium bicarbonate wherein esomeprazole magnesium trihydrate is comprised in 20 mg or 40 mg based on the weight of esomeprazole, and sodium bicarbonate is comprised in 800 mg.

The composition according to the present invention may be formulated in a pellet, capsule, tablet comprising a monolayered tablet, bilayered tablet, and inner-core tablet, or granule, which is not limited thereto.

The formulation according to the present invention may be prepared based on a method for preparing any oral solid dosage as known in the art, specifically, a granule, pellet, capsule, or tablet.

Advantageous Effects of Invention

The present invention relates to a pharmaceutical composition with improved stability comprising omeprazole, its enantiomer, or its pharmaceutically acceptable salt, and sodium bicarbonate. The pharmaceutical composition according to the present invention has improved stability and provides improved dissolution rate and bioavailability with reduced side effects by comprising a low dose of sodium bicarbonate.

BRIEF DESCRIPTION OF DRAWINGS

FIG. 1 shows the results of the analysis on the assay of esomeprazole and omeprazole according to pH.

FIG. 2 shows the results where the pH of simulated gastric juice was measured according to the dose of sodium bicarbonate.

FIG. 3 shows the results of the dissolution test on the formulations of Example 1 and Comparative Example 1.

FIG. 4 shows the results of the blood concentration change of esomeprazole in the test drug and the reference drug.

FIG. 5 shows the results where the change of pH in the stomach was measured after the single dose and the repeated doses for each of the test drug and the reference drug.

BEST MODE FOR CARRYING OUT THE INVENTION

Hereinafter, the present invention will be more detailed through the following examples. However, the examples are merely provided for a better understanding of the present invention for the purpose of illustration, but are not to be construed as the limitation of the claimed scope.

EXAMPLE 1

Preparation of a Tablet of Esomeprazole Comprising Sodium Bicarbonate

A tablet comprising esomeprazole and sodium bicarbonate was prepared according to the following method.

1. First Coating

Hydroxypropyl cellulose was added and dissolved in purified water, followed by adding arginine, simethicone, purified water, esomeprazole magnesium trihydrate (22.3 mg; 20.00 mg based on the weight of esomeprazole), magnesium oxide, and talc, and dispersing them, to prepare a coating solution. Sugar spheres were put into a fluidized bed granulation-coating machine, spraying the coating solution, to prepare a first pellet.

2. Second Coating

Polyvinyl alcohol, talc, titanium oxide, glycerol monocaprylocaprate, and sodium lauryl sulfate were added and dispersed in purified water to prepare a coating solution.

The coated materials from the first coating process were put into a fluidized bed granulation-coating machine, spraying the coating solution, to prepare a second pellet.

3. Blending and Tableting

The second pellet, sodium bicarbonate (800 mg), copovidone, and crospovidone were put in a mixer to be mixed, followed by adding sodium stearyl fumarate and lubricating to prepare granules. The prepared granules were tableted.

4. Third Coating

Polyvinyl alcohol, talc, titanium oxide, glycerol monocaprylocaprate, sodium lauryl sulfate, red iron oxide, black iron oxide, and yellow iron oxide were added in purified water to prepare a coating solution. The core tablets were put into a coating machine, spraying the coating solution, coating, and drying to obtain the final film coated tablet.

COMPARATIVE EXAMPLE 1

Preparation of a Tablet of Esomeprazole which Does Not Comprise Sodium Bicarbonate A tablet of esomeprazole which does not comprise sodium bicarbonate was prepared according to the following method.

1. First Coating

Hydroxypropyl cellulose was added and dissolved in purified water, followed by adding arginine, simethicone, purified water, esomeprazole magnesium trihydrate, magnesium oxide, and talc, and dispersing them, to prepare a coating solution. Sugar spheres were put into a fluidized bed granulation-coating machine, spraying the coating solution, to prepare a first pellet.

2. Second Coating

Polyvinyl alcohol, talc, titanium oxide, glycerol monocaprylocaprate, and sodium lauryl sulfate were added and dispersed in purified water to prepare a coating solution. The first coated materials were put into a fluidized bed granulation-coating machine, spraying the coating solution, to prepare a second pellet.

3. Blending and Tableting

The second pellet, lactose, microcrystalline cellulose, copovidone, and crospovidone were put in a mixer to be mixed, followed by adding sodium stearyl fumarate and lubricating to prepare granules. The granules were tableted.

4. Third Coating

Polyvinyl alcohol, talc, titanium oxide, glycerol monocaprylocaprate, sodium lauryl sulfate, red iron oxide, black iron oxide, and yellow iron oxide were added in purified water to prepare a coating solution. The core tablets were put into a coating machine, spraying the coating solution, coating, and drying to obtain the final film coated tablet.

TEST EXAMPLE 1

Stability Test of Esomeprazole and Omeprazole According to pH

The esomeprazole solution and the omeprazole solution, which are at a concentration of 20 mg/mL, were respectively added in 2 mL into 100 mL of a buffer solution, followed by analyzing the concentration of esomeprazole and omeprazole according to pH based on the analysis method as follows:

<Analysis method>
A) Detector: UV-Visible spectrophotometer (measurement wavelength:280 nm)
B) Column: Inertsil C8-3 (4.6×150 mm, 5 μm) or equivalent column
C) Injection amount: 20 μl
D) Flow rate: 1.5 mL/min
E) Column temperature: Constant temperature near 40° C.
F) Sample temperature: Constant temperature near 10° C.
G) Analysis time: 6 minutes
H) Mobile phase: Buffer solution at pH 7.6 and acetonitrile (65:35)

The buffer solution at pH 7.6 was prepared as follows: 0.725 g of sodium dihydrogen phosphate monohydrate ($NaH_2PO_4 \cdot H_2O$) and 4.472 g of anhydrous disodium hydrogen phosphate ($Na_2HPO_4$) were weighed to be put in an 1 L volumetric flask and dissolved in purified water, followed by filling the flask with purified water up to the calibration mark. 250 mL of the liquid was taken to be put in an 1 L volumetric flask, followed by filling the flask with purified water up to the calibration mark and adjusting the pH to 7.6 with phosphoric acid.

The analysis results were shown in Table 1 below and FIG. 1.

TABLE 1

|  |  | 5 min | 10 min | 15 min | 30 min | 45 min | 60 min | 120 min |
|---|---|---|---|---|---|---|---|---|
| pH 4.0 | S-omeprazole | 64.1 | 31.0 | 15.9 | 6.9 | 1.7 | 0.9 | 0.1 |
|  | Omeprazole | 57.2 | 29.4 | 15.3 | 6.7 | 1.6 | 0.8 | 0.1 |
| pH 6.0 | S-omeprazole | 74.4 | 72.8 | 71.0 | 68.9 | 66.3 | 63.6 | 54.9 |
|  | Omeprazole | 74.9 | 74.2 | 71.7 | 69.6 | 65.4 | 64.1 | 55.1 |
| pH 6.8 | S-omeprazole | 95.6 | 90.8 | 90.5 | 89.7 | 88.9 | 88.3 | 86.2 |
|  | Omeprazole | 91.5 | 90.5 | 89.9 | 89.8 | 88.8 | 88.3 | 85.5 |
| pH 7.0 | S-omeprazole | 99.6 | 99.0 | 99.3 | 98.9 | 98.7 | 98.1 | 96.8 |
|  | Omeprazole | 100.5 | 99.0 | 98.9 | 98.2 | 97.9 | 97.5 | 95.8 |
| pH 7.3 | S-omeprazole | 100.1 | 100.1 | 100.0 | 100.0 | 100.0 | 100.0 | 99.90 |
|  | Omeprazole | 99.8 | 100.0 | 99.9 | 99.8 | 99.8 | 99.8 | 99.86 |
| pH 7.5 | S-omeprazole | 99.4 | 99.3 | 99.2 | 99.1 | 99.3 | 99.1 | 98.2 |
|  | Omeprazole | 100.5 | 99.7 | 99.7 | 99.4 | 99.2 | 98.9 | 98.2 |
| pH 8.0 | S-omeprazole | — | — | 101.1 | 100.9 | 100.7 | 100.7 | 100.0 |
|  | Omeprazole | — | — | 99.7 | 99.6 | 99.5 | 99.5 | 98.6 |

As shown in Table 1 above, it was confirmed that esomeprazole and omeprazole are stable for at least 2 hours in case of pH 7.0 or more.

TEST EXAMPLE 2 pH Test of Simulated Gastric Juice According to the Dose of Sodium Bicarbonate

To determine the dose of sodium bicarbonate, the conditions on drug release and gastric juice were set as follows: in particular, 1) the amount of gastric juice in a fasting condition is generally 20 to 50 mL; 2) the amount of gastric juice secretion is about 2 L/day (about 83 mL/hr); 3) the total amount of gastric juice that reacts with a drug (formulation) is assumed as about 200 mL; and 4) a drug is taken with water where the water amount is 200 mL.

A pH was measured according to the change of the dose of sodium bicarbonate in a solution (37° C.) where 200 mL of purified water was put in 200 mL of simulated gastric juice. The measurement results were shown in Table 2 below and FIG. 2.

TABLE 2

| sodium bi-carbonate (mg) | | | | | | | | |
|---|---|---|---|---|---|---|---|---|
| 500 | 600 | 700 | 800 | 900 | 1,000 | 1,100 | 1,200 | 1,300 |
| pH 5.77 | 6.51 | 7.30 | 7.30 | 7.31 | 7.37 | 7.38 | 7.38 | 7.40 |

As shows in Table 2 above, it was confirmed that as the dose of sodium bicarbonate increased, the pH value increased. Further, few changes of the pH value were found in 1,000 mg or more of sodium bicarbonate.

It was also confirmed that the dose of sodium bicarbonate that can neutralize 200 mL of simulated gastric juice to show neutral pH was at least 600 mg.

TEST EXAMPLE 3

Dissolution Test of a Formulation According to the Presence or Absence of Sodium Bicarbonate Dissolution test on the formulations of Example 1 and Comparative Example 1 was performed where the conditions on the dissolution test and analysis were as follows:

<Dissolution Test Condition>
1) Dissolution method: Korean Pharmacopoeia General test, Dissolution tests, Method 3 (Flow Through Cell Method)
2) Dissolution medium: pH 1.2→pH 4.0
3) Dissolution temperature: 37±0.5° C.
4) Flow rate: 2 mL/min
5) Test time: pH 1.2 (15 min)→pH 4.0 (15 min)
<Analysis Condition>
1) Detector: UV spectrophotometer (measurement wavelength:302 nm)
2) Column: Capcell Pak C18 (4.6×150 mm, 5 μm) or equivalent column
3) Injection amount: 20 μL
4) Flow rate: 1.0 mL/min
5) Column temperature: Constant temperature near 30° C.
6) Sample temperature: Constant temperature near 10° C.

7) Mobile phase: Acetonitrile, a buffer solution at pH 7.3, and water (350:500:150)

The buffer solution at pH 7.3 was prepared as follows: 1 mol/L sodium dihydrogen phosphate solution and 0.5 mol/L disodium hydrogen phosphate solution were taken in 10.5 mL and 60 mL, respectively, to be put in an 1 L volumetric flask, followed by filling the flask with purified water up to the calibration mark.

The results of the dissolution test were shown in Table 3 below and FIG. 3.

TABLE 3

| Dissolution rate (ng/mL) | Example 1 | Comparative Example 1 |
|---|---|---|
| 5 min | 4,462,741 | 22,929 |
| 10 min | 3,696,359 | 8,566 |
| 15 min | 3,074,658 | 4,585 |
| 20 min | 1,954,877 | 2,185 |
| 25 min | 1,189,882 | 835 |
| 30 min | 786,910 | 9,793 |

As shows in Table 3 above, Comparative Example 1 that does not comprise sodium bicarbonate showed a very low dissolution rate, from which it was confirmed that it was rarely dissolved. Meanwhile, Example 1 comprising sodium bicarbonate showed hundreds to thousands of times higher of a dissolution rate than Comparative Example 1, especially, the highest dissolution rate at 5 minutes after the administration. As such, it was confirmed that it was rapidly dissolved.

TEST EXAMPLE 4

Blood Concentration of Esomeprazole

A test drug (a tablet prepared according to Example 1) and a reference drug (Nexium® tablet 20 mg as currently marketed) were taken as repeated once-daily doses for seven days at a fasting condition to measure the change on a blood concentration of esomeprazole and AUC according to the time, which were shown in Table 4 below and FIG. 4.

TABLE 4

| AUC (h · ng/mL) | |
|---|---|
| Reference drug | Test drug |
| 2578.09 | 2802.25 |

As shown in Table 4 above, the test drug had a higher AUC than the reference drug. Further, as shown in FIG. 4, it was confirmed that upon administration, the test drug, in comparison with the reference drug as an enteric-coated formulation, was immediately dissolved and absorbed to show a higher blood concentration after administration. Since it is important in view of the nature of the disease to exert immediate treatment effect, it was confirmed that the test drug shows the remarkably superior effect to the reference drug.

In comparison with the reference drug, the test drug showed a higher blood concentration for up to 2 hours and a similar blood concentration after 2 hours. As such, it was confirmed that the test drug has an improved bioavailability.

TEST EXAMPLE 5

Change of pH in the Stomach

A test drug (a tablet prepared according to Example 1) and a reference drug (Nexium® tablet 20 mg as currently marketed) were taken as a single dose and as repeated doses for seven days to measure the change of pH in the stomach. The time holding gastric pH≤4 was measured while observing for 24 hours after administration. The results were shown in Table 5 below and FIG. 5.

TABLE 5

| | Percent (%) of time with gastric pH ≤4 for 24 hours interval after single dose, repeated doses | |
|---|---|---|
| | Test drug | Reference drug |
| Baseline | 80% | 80% |
| Single dose | 43.20% | 44.49% |
| Repeated doses | 30.07% | 29.84% |

The single dose of the reference drug and the test drug reduced the time holding gastric pH≤4 from about 80% to 44.49% and 43.20%, respectively, in comparison with the baseline. The repeated doses of the reference drug and the test drug showed 29.84% and 30.07%, respectively. As such, it was confirmed that the time holding gastric pH≤4 was all similar in cases of the baseline, single dose, and repeated doses.

In sum, a formulation according to the present invention has a higher value on the initial release, absorption, and blood concentration of a drug in comparison with an enteric-coated formulation, and thus exerts an improved bioavailability and treatment effect of a gastric acid-related disease.

The invention claimed is:

1. A tablet comprising:
   20 mg or 40 mg of a magnesium salt of esomeprazole based on the weight of esomeprazole; and
   800 mg of sodium bicarbonate;
   wherein:
   the magnesium salt of esomeprazole is in the form of a plurality of pellets or granules;
   the pellets or granules do not comprise the sodium bicarbonate;
   the pellets or granules are coated with a coating agent;
   the sodium bicarbonate does not contact the magnesium salt of esomeprazole in the tablet; and
   the tablet dissolves at pH 1.2.

2. The tablet according to claim 1, wherein the magnesium salt of esomeprazole is esomeprazole magnesium trihydrate.

3. The tablet according to claim 1, wherein the coating agent separates the sodium bicarbonate from the magnesium salt of esomeprazole.

4. The tablet according to claim 1, wherein the coating agent does not comprise sodium bicarbonate.

* * * * *